(12) United States Patent
MacAndrew et al.

(10) Patent No.: US 6,286,506 B1
(45) Date of Patent: *Sep. 11, 2001

(54) INHALATION DEVICE

(75) Inventors: John MacAndrew, St. Neots; William Revell, Sudbury; Paul Robertson, Chrishall, all of (GB); Elna Berg, Dalby; Magnus Jeppsson, Lund, both of (SE)

(73) Assignee: Astra Aktiebolag, Sodertalje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,777
(22) PCT Filed: Sep. 23, 1996
(86) PCT No.: PCT/SE96/01184
  § 371 Date: Sep. 4, 1997
  § 102(e) Date: Sep. 4, 1997
(87) PCT Pub. No.: WO97/11732
  PCT Pub. Date: Apr. 3, 1997

(30) Foreign Application Priority Data

Sep. 27, 1995 (SE) .................................................. 9503344

(51) Int. Cl.[7] .................................................. A61M 15/00
(52) U.S. Cl. .................................................. 128/203.15
(58) Field of Search .................. 128/203.15, 200.23, 128/200.18, 200.22, 203.12; 222/631, 634, 527

(56) References Cited

U.S. PATENT DOCUMENTS

| | | | |
|---|---|---|---|
| 3,636,949 | * 1/1972 | Kropp | 128/200.23 |
| 4,674,491 | * 6/1987 | Brugger et al. | 128/203.15 |
| 5,074,294 | 12/1991 | Chiesi . | |
| 5,435,301 | * 7/1995 | Herold et al. | 128/203.15 |
| 5,579,760 | * 12/1996 | Kohler | 128/203.15 |
| 5,823,183 | * 10/1998 | Casper et al. | 128/203.15 |

FOREIGN PATENT DOCUMENTS

| | | | |
|---|---|---|---|
| 7202591 | * 9/1991 | (AU) | 128/203.15 |
| 699313 | * 12/1964 | (CA) | 128/200.23 |
| 0 069 715 | 1/1983 | (EP) . | |
| 0 237 507 | 9/1987 | (EP) . | |
| 0546996 | * 6/1993 | (EP) | 128/203.15 |
| 1 565 029 | 4/1980 | (GB) . | |
| 92/04066 | 3/1992 | (WO) . | |
| 92/04069 | 3/1992 | (WO) . | |
| WO 92/04066 | 3/1992 | (WO) . | |
| WO 94/11043 | 5/1994 | (WO) . | |
| 96/19253 | 6/1996 | (WO) . | |
| 97/11732 | 4/1997 | (WO) . | |

OTHER PUBLICATIONS

Deposition and Clinical efficacy of terbutaline sulphate from "Turbuhaler" . . . , Newman et al, Eur. Respir.J., 1989, 2, 247–252.*

Optimal Inhalation Technique with terbutaline "Turbuhaler", Hansen et al, Eur. Respir. J., 1989, 2, 637–639.*

PCT Search Report.

* cited by examiner

*Primary Examiner*—Aaron J. Lewis
(74) *Attorney, Agent, or Firm*—Fish & Richardson, P.C.

(57) ABSTRACT

An inhalation device for use with an inhaler is disclosed. The device includes a dispersion chamber constructed for fluid communication with the inhaler and a suction chamber of variable internal volume in fluid communication with the dispersion chamber. The internal volume of the suction chamber can be increased during use, producing a negative pressure in the dispersion chamber, thereby drawing a substance to be inhaled from the inhaler into the dispersion chamber for subsequent inhalation.

30 Claims, 10 Drawing Sheets

INHALATION DEVICE

BACKGROUND

The present invention relates to a device for inhalation of a pharmaceutically active substance comprising means for generating a negative pressure or vacuum and to a method by which any suitable substance may be prepared in a dispersed state.

Inhalable pharmaceutically active substances are generally used for the treatment of diseases in the bronchial and pulmonary area, such as asthma and chronic bronchitis. Various types of inhalation devices or apparatus are used for this purpose.

One type of inhalation device is the breath-actuated inhaler, particularly but not necessarily a dry powder inhaler, containing multiple doses of a medicament containing an active substance. The inhaler has a manoeuvring means comprising a manoeuvring element for loading one dose of the medicament to a dosing unit and providing said dose in a position for inhalation. An inhaler of the prescribed type is described in EP-A-0 069 715 and EP-A-0 237 507.

The function of this type of known device depends on the creation of an airflow through the inhalation device resulting from inhalation by the patient. The airflow causes the active substance to be moved from a release position in a dosing unit into the airflow in which it is dispersed. A break down of aggregated particles must also be achieved during inhalation, because aggregates always occur in powders having fine particles, especially finely divided powders of the type generally used for inhalation. A particularly advantageous inhaler of the above mentioned type is the dry-powder, breath-actuated, multi dose inhaler TURBUHALER®, generally described in the above mentioned EP-patents.

Some patients such as small children and elderly people with diseases in the bronchial area are not able to use breath-actuated inhalers as it can be hard or even impossible for these patients to achieve the necessary inhalation flow. Airflow needed is about 30–60 l/min and many patients such as small children and elderly people are not capable of producing the necessary inhalation flow. These patients have to use inhalers with pressurised gas, i.e. freon CFC. Such inhalers suffer from many known disadvantages, such as unwanted side effects both for the environment and the patients.

In order to facilitate the inhalation of pharmaceutically active substances which are administered by the use of pressurised metered dose inhalers, so called pMDI:s, it is known to provide dispersion chambers having a considerable volume, e.g. up to 2000 ml, into which the substance, with the pressurised gas, is dispersed. These devices are generally called "spacers" and a typical spacer is known from GB 1 565 029.

Inhalation devices including dispersion chambers have also been developed for breath-actuated, dry-powder inhalers of the above mentioned type. Such an inhalation device is described in EP-A-0 548 152. This device comprises a reservoir for the active substance (this can be part of a dry powder inhaler arranged inside the inhalation device) and a dispersion chamber. The dispersion chamber has a movable wall part which varies the volume of the dispersion chamber between minimum and maximum volumes so as to draw active substance into the dispersion chamber from the dry powder inhaler. The movement of the movable part is achieved by the movement of a piston which when lowered creates a negative pressure within the dispersion chamber. The active substance is thereby drawn out into the chamber. A patient may then inhale the dispersed substance in the dispersion chamber through a face mask or mouth piece. This device is complicated and difficult to use. Furthermore, contact with powder and the design of several mechanical parts make the function of the device less reliable.

SUMMARY OF THE INVENTION

It is therefore an object of the present invention to provide an inhalation device including a dispersion chamber which can be used by patients having reduced ability and which can create the air flow necessary to lift a dose from a release position into an inhalation channel, disperse it in the air flow and achieve the required break up of aggregated particles when using a breath-actuated inhaler. Preferably, the device should be simple and reliable to activate for inhalation and to use. The device should preferably be light, robust and attractive to take with you, since patients, for example asthma sufferers, always have to have their devices available.

According to the present invention, there is provided an inhalation device for use with an inhaler, the inhaler being for providing a dose of a substance for inhalation, the device having:

a section for receiving the inhaler;

a dispersion chamber in fluid connection with said section; and a suction chamber of variable internal volume and in fluid connection with said dispersion chamber; wherein by increasing the internal volume of said suction chamber, a negative pressure is produced in said dispersion chamber, thereby drawing substance from the inhaler into the dispersion chamber for subsequent inhalation.

According to the present invention, there is also provided an inhalation device having:

an inhaler for providing a dose of a substance for inhalation;

a dispersion chamber in fluid connection with said inhaler; and a suction chamber of variable internal volume and in fluid connection with said dispersion chamber; wherein by increasing the internal volume of said suction chamber, a negative pressure is produced in said dispersion chamber, thereby drawing substance from the inhaler into the dispersion chamber for subsequent inhalation.

The significance of this is that the substance for inhalation does not come into contact with any parts of the suction chamber creating the negative pressure. Furthermore, the dispersion chamber may have fixed simple internal surfaces which minimize retention of substance. Preferably, the suction chamber displaces a smaller volume than the volume of the dispersion chamber and is connected to the dispersion chamber substantially at an opposite end to the connection with the inhaler. In this way, dispersed substance drawn into the dispersion chamber does not reach the connection to the suction chamber.

Further preferred features are described in the appended claims.

Thus, there may be provided an inhalation device which facilitates the use of especially a TURBUHALER® for patients presently having to use pressurised metered-dose inhalers.

The device according to the invention may be especially designed for patients who are not capable of using a breath actuated inhaler of the above mentioned type for the reason that they are not capable of creating the inhalation flow necessary to release and lift the dose of the substance into the inhalation channel and to the lungs.

It is also an object of the present invention to provide a method of preparing a substance in a dispersed state.

According to the present invention, there is also provided a method of preparing a substance in a dispersed state in a dispersion chamber by drawing the substance into the dispersion chamber from a dispenser, wherein a suction chamber of variable internal volume is provided in fluid connection with the dispersion chamber and the method includes the steps of:

increasing the internal volume of the suction chamber so as to produce a negative pressure in said dispersion chamber to thereby draw said substance from the dispenser into the dispersion chamber.

As mentioned above, inhalation devices, including those with expandable dispersion chambers, can include moveable parts which allow a substance to be sucked into a dispersion chamber. Of course, these parts may be operated manually with the force for filling the dispersion chamber being provided directly by the user. However, this force is preferably provided by a sprung device such that the user merely has to release the tension in the device. Unfortunately, however, due to the very nature of elasticity, the force provided by a spring decreases as the spring expands. Thus the gas flow into the dispersion chamber is much higher for the first part of the filling of the chamber. This is particularly undesirable when the gas flow is used to pick up the substance from an inhaler, for instance to pick up dry powder and disperse it in the gas.

According to the present invention, there is provided an inhalation device comprising:

a dispersion chamber for containing a substance dispersed in a gas;

a sprung device for creating a change in pressure so as to cause said dispersed substance to flow into said dispersion chamber; and a flow regulating valve of variable restriction for restricting said flow of said dispersed substance into said dispersion chamber; wherein the restriction of said flow regulating valve is arranged to vary in conjunction with operation of said sprung device so as to compensate for characteristics of the sprung device.

In order to restrict or regulate the flow, the valve may be located anywhere in the fluid path, i.e. in the inlet or outlet of the dispersion chamber or upstream or downstream thereof.

The position, construction and characteristics of the valve should be chosen according to the type of inhalation device, the characteristics of the sprung device and the substance. In general though, a sprung device will tend to create a much higher flow into the dispersion chamber during the first part of the its operation than during its last part. Therefore, the flow regulating valve should be designed to compensate for this and offer the most restriction during the first part of the operation of the sprung device. For instance, where the sprung device includes a piston moveable from a first to a second position, the restriction should decrease as the piston moves from the first to the second position.

In any device with a dispersion chamber, including those of the prior art using an expandable dispersion chamber, some of the dispersed substance can fall out of its suspended state in the gas and collect on internal surfaces of the dispersion chamber. If the user then tips the device, the collected substance, which might be powder or liquid, can be poured out of the dispersion chamber outlet and, if fitted, a mouthpiece. This is undesirable.

According to the present invention, there is provided an inhalation device for providing a substance dispersed in a gas for inhalation, the device comprising:

walls defining a dispersion chamber for containing said dispersed substance and defining an outlet in said dispersion chamber through which said dispersed substance may leave said dispersion chamber in a dispersed state; wherein said walls also define at least one channelled region at least partly surrounding said outlet such that any substance on said walls cannot be caused to travel across the walls defining said channelled region and to pass through said outlet.

The channelled region may be provided as an inwardly extending funnel or cone or merely as an inwardly extending pipe. The important aspect is that, if the user turns the device upside down, any substance which has collected on the sides will travel along the walls and into the channelled region rather than out through the outlet. Since the outlet is positioned inwardly of the general periphery of the chamber, substance cannot be poured out of it.

The inhalation device according to the present invention will now be described by way of example with reference to the accompanying drawings:

BRIEF DESCRIPTION OF THE DRAWINGS

FIG. 1 is a side view of an inhalation device when the device is retracted and closed in its inactive position, FIG. 2 shows the first step of the activation of the device, FIG. 3 shows the inhalation device of FIG. 1 in position for inhalation, FIG. 4 shows schematically the flow of the air when the substance is released and dispersed in the dispersion chamber just after the device has been activated for inhalation, FIG. 5 shows a device with a preferred mouthpiece valve, FIGS. 6*a–c* show components of a mouthpiece valve, FIGS. 7*a–f* show various flow regulating valves, FIG. 8*a* is a view along lines IV—IV in FIG. 1 in the first step of activation of the device corresponding to FIG. 2, FIG. 8*b* is a view along lines IV—IV in FIG. 1 in the position where the spacer has been activated and the dose released corresponding to FIG. 3, FIG. 9 shows a gear linkage for the mounting element of the device, FIG. 10 shows a device with an insert to prevent collected powder falling out, FIGS. 11*a* and 11*b* show variations of the insert of FIG. 10.

DESCRIPTION OF THE PREFERRED EMBODIMENTS

The inhalation device comprises a housing 1 containing a first chamber 2, in which a suction chamber of variable volume is formed, and a second chamber 3, the dispersion chamber, having a constant volume. In the preferred embodiment the chambers are cylindrical but any other form is possible. The two chambers 2 and 3 are arranged axially and telescopically movable in relation to each other and a fluid connection is provided between the two chambers.

The second, or dispersion, chamber 3 is provided with a lid 31 covering its upper part. The lid 31 may be a separate component or formed integrally with the chamber 3. Said lid 31 is provided with a mouth piece 32 intended to be inserted into the mouth of the user when the device is to be used. The mouthpiece is preferably detachable from the lid 31 for instance by means of a bayonet fitting. In this way, it may be removed for cleaning.

Figure 1:
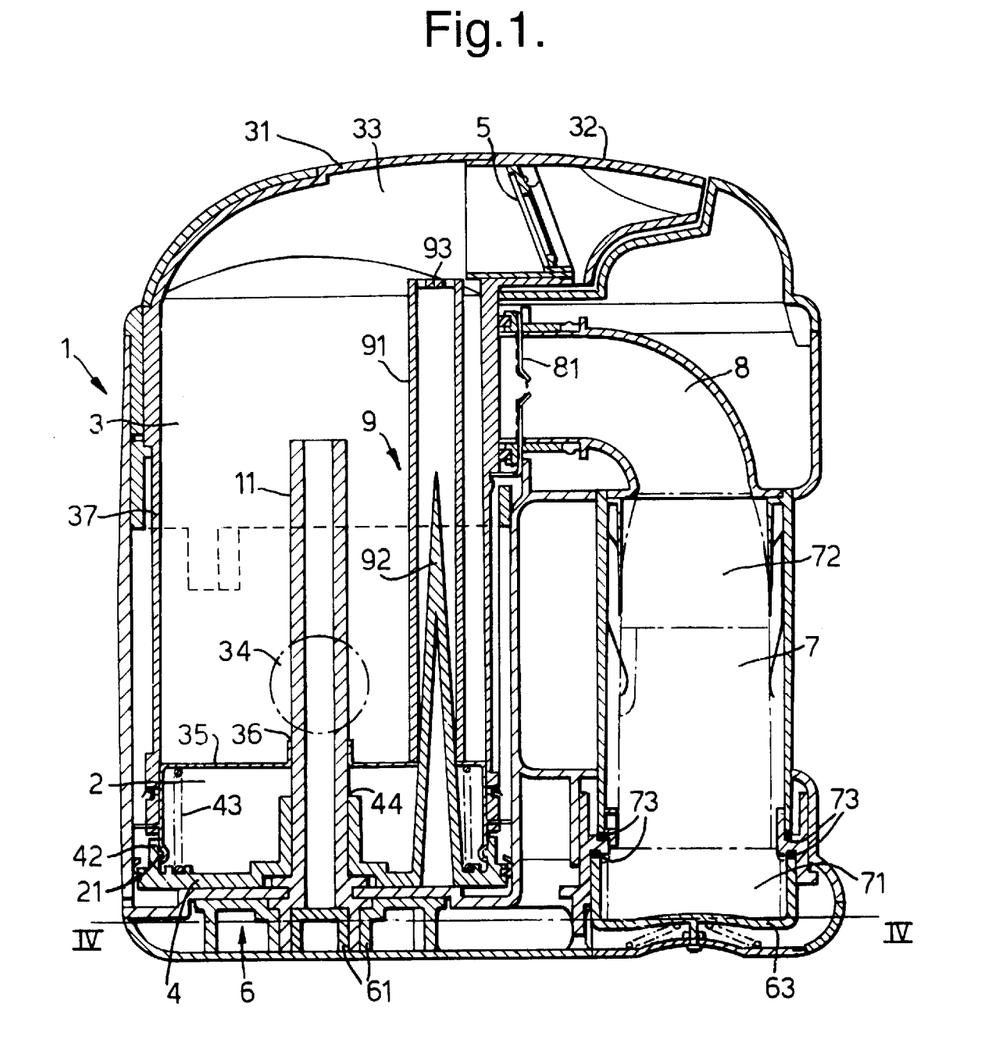
Figure 2:
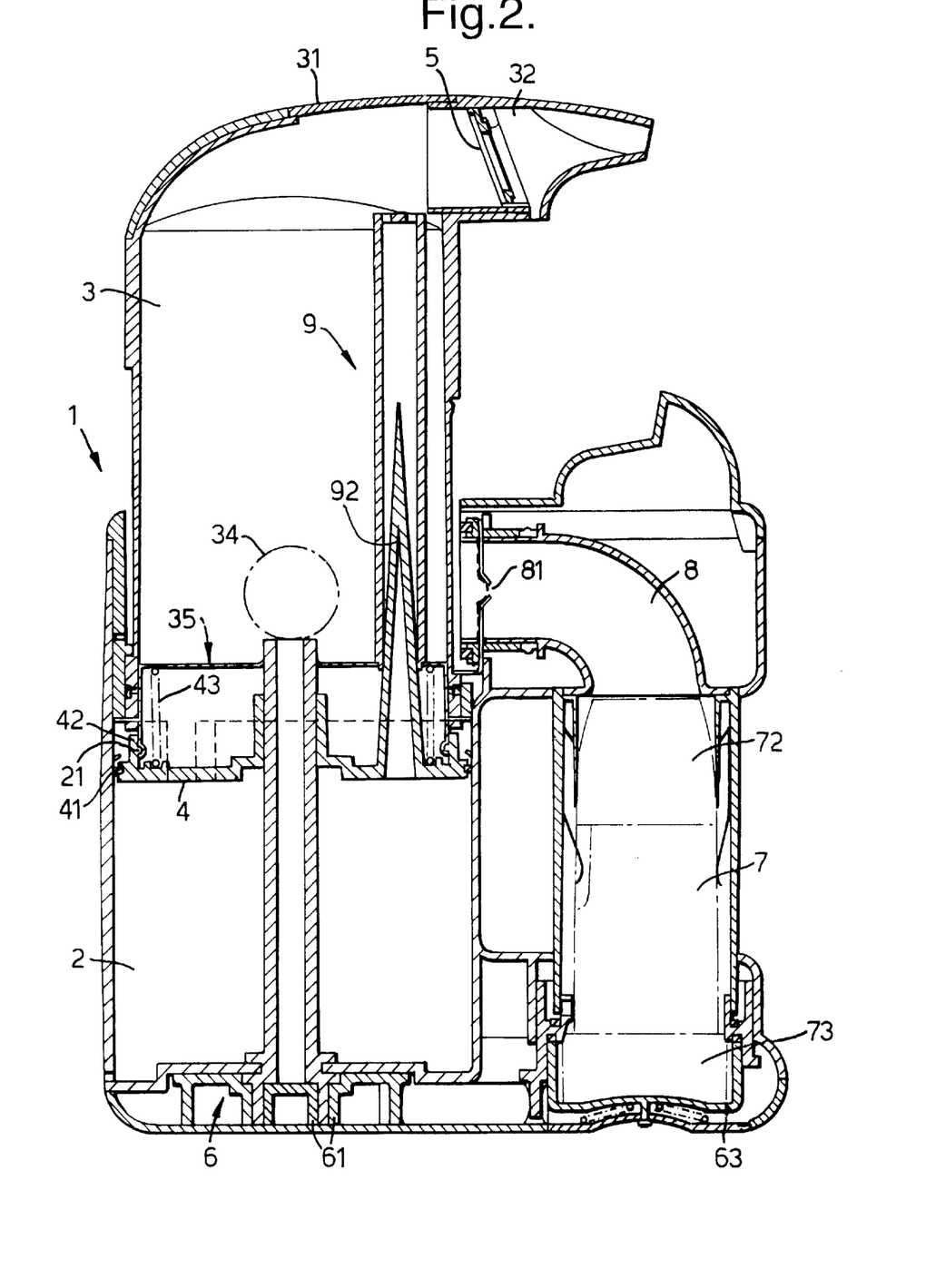
Figure 3:
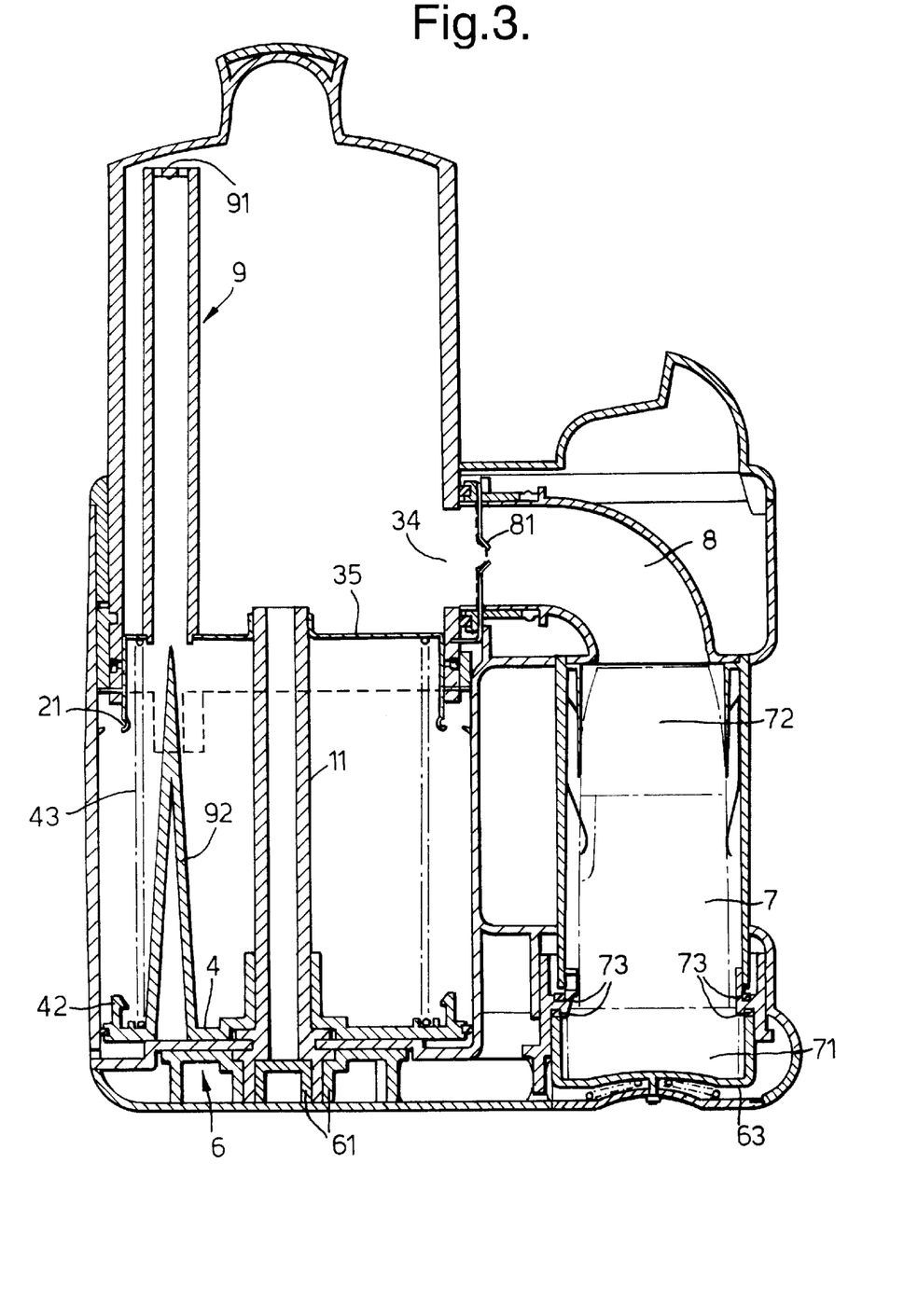
Figure 4:
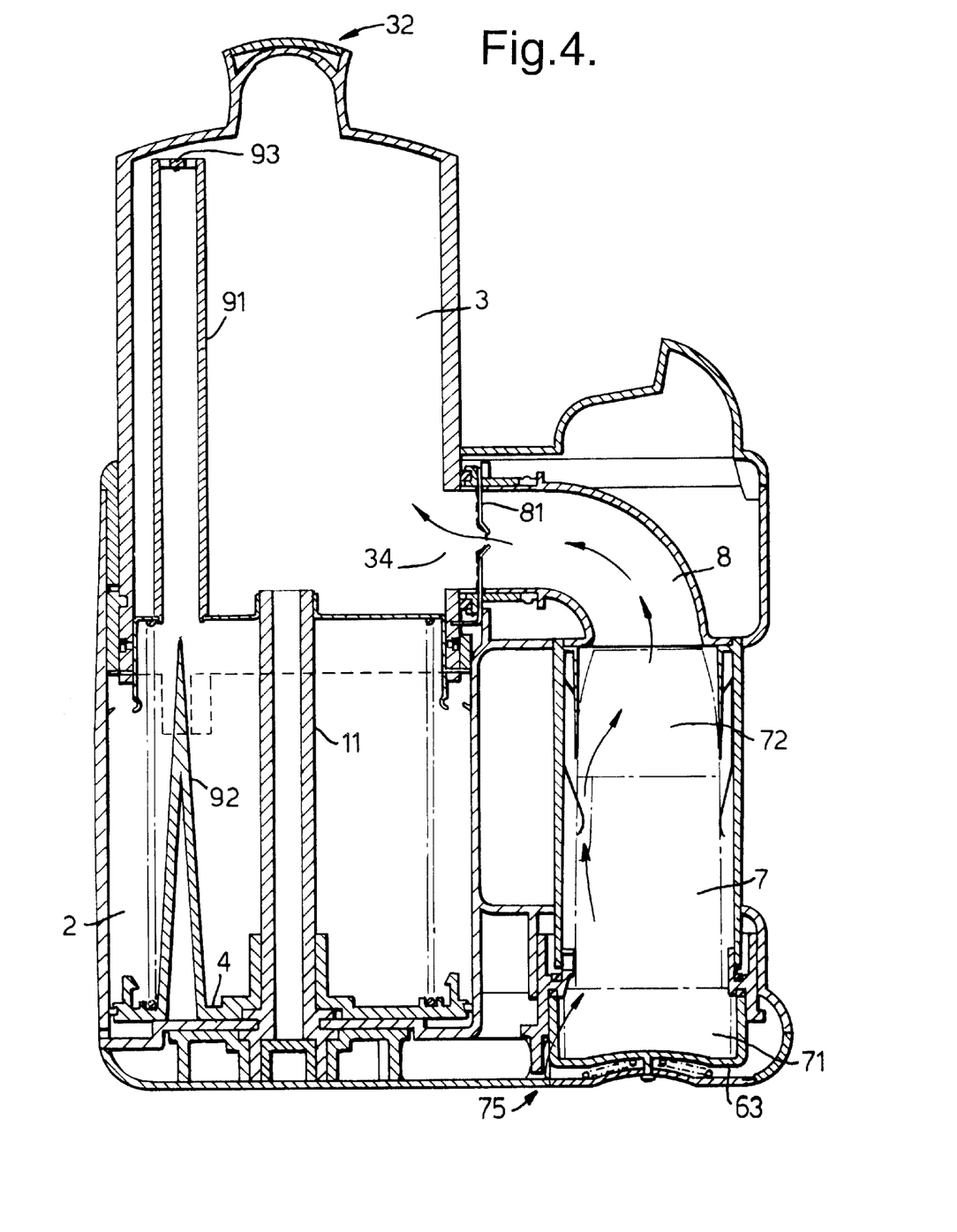

Inside the lid, an inhalation channel 33 is arranged between and in fluid connection with the dispersion chamber 3 and the mouth piece 32. When the device is to be used, said mouth piece is moved between a retracted position as can be seen in FIGS. 1 and 2 and an active position as can be seen in FIGS. 3 and 4. If an infant is to use the inhalation device a face mask of any known kind can be mounted on the mouth piece or the mouth piece can be exchanged for such a face mask.

A one way valve 5 is provided in said inhalation channel 33. When the device is used and the user inhales through the mouth piece 32, the valve opens in order to let the inhalation air enter through the mouth piece into the mouth of the user. When the user exhales, the valve 5 closes in order to prevent exhalation air to enter into the channel and the dispersion chamber 3. In the preferred embodiment, the one way valve 5 is a so called flap valve, but any other type of valve could be used, such as a torpedo or ball valve.

Figure 5:
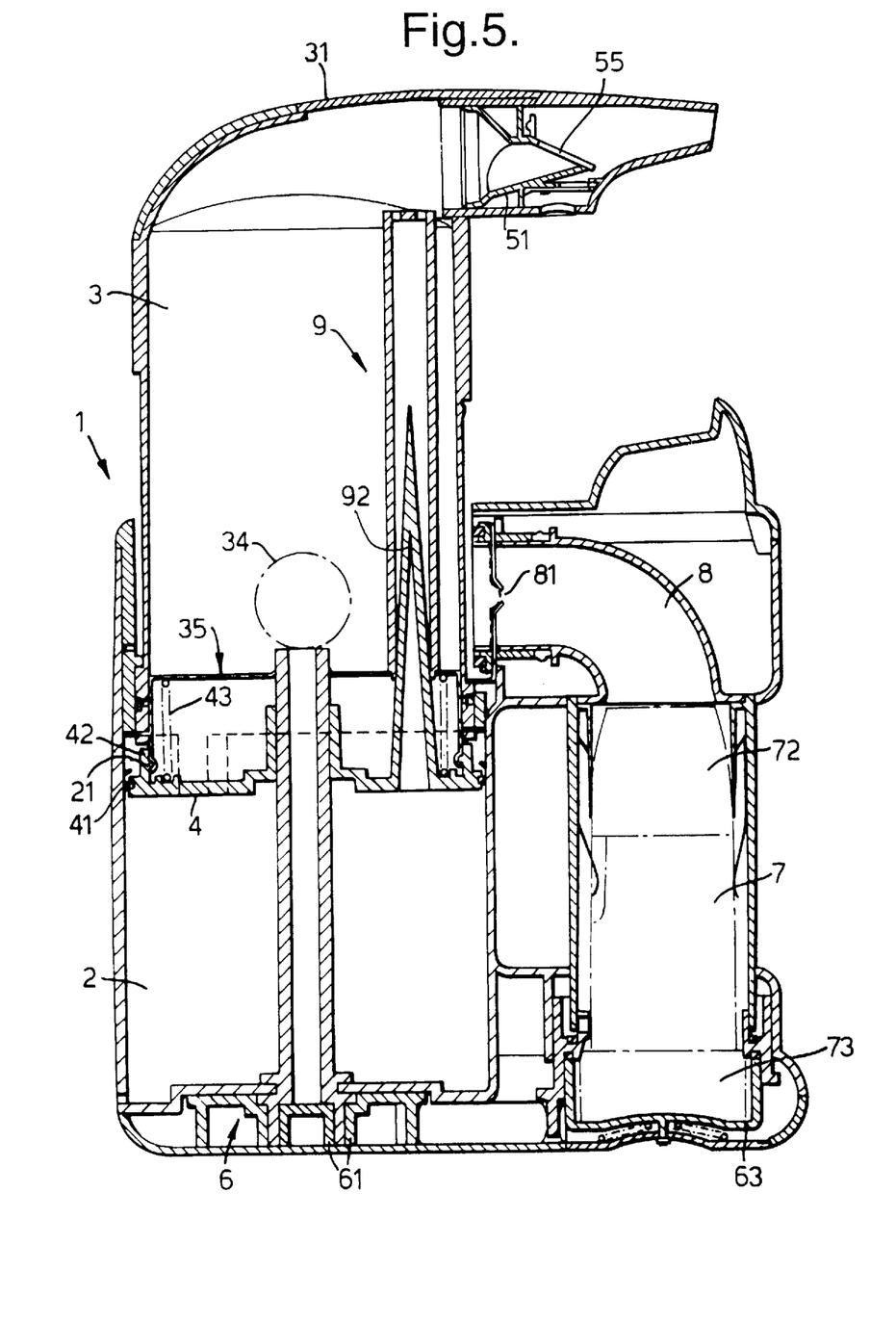
Figure 6A:
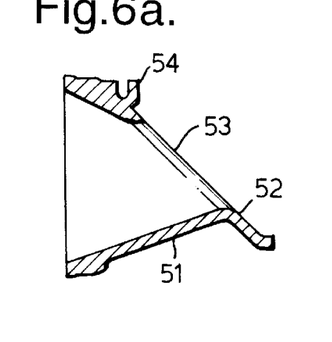
Figure 6B:
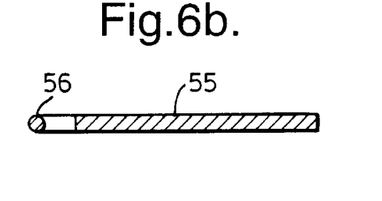
Figure 6C:
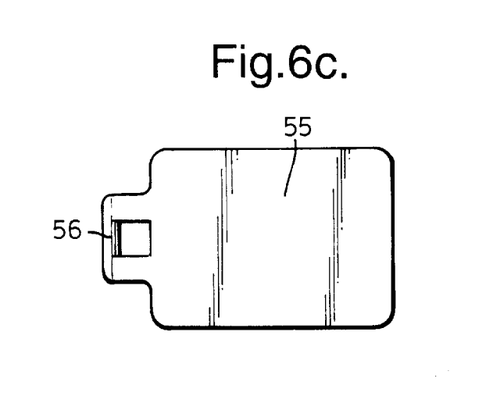

FIG. 5 shows a device with a preferred mouthpiece valve and FIGS. 6a to 6c illustrate the components of a similar valve. The valve comprises an insert 51 having a valve seat 52, an aperture 53 and a bearing 54. The valve flap 55 shown in FIGS. 6b and 6c comprises a shaft 56 for insertion into bearing 54 such that the flap may freely rotate. When the insert 51 is fitted in the mouthpiece, the wall of the mouthpiece closes bearing 54.

Inside the housing 1, means 6 are provided for mounting and activating an inhaler 7 which may be an internal part of or detachably mounted in the housing 1. In the preferred embodiment, the inhaler is of the type sold under the trademark TURBUHALER® and is mounted in a chamber provided adjacent chamber 2. The inhaler 7 comprises a reservoir for the substance to be inhaled, a dosing unit provided in the inhalation channel of the inhaler, manoeuvring means 71 for feeding a dose of the substance to the dosing unit and to place it in position for inhalation in the inhalation channel and a mouth piece 72. Although the inhaler is a TURBUHALER® in the preferred embodiment any other inhaler of this or similar types could be placed in a device according to the invention.

The manoeuvring means 71 of the inhaler 7 is mounted in a mounting and activating means 6 of the inhalation device in a manner which will be described in more detail below.

When mounted in the housing 1, the mouth piece 72 of the inhaler 7 is connected to the dispersion chamber 3 via the first end of a substantially L-shaped channel 8. When the device is ready for inhalation, the other end of the channel 8 is arranged to be in fluid connection with the dispersion chamber 3 via an opening 34 provided in the wall 37 of the dispersion chamber 3. A seal 81 is arranged close to the end of the channel 8. When the device is in its retracted position, the opening 34 is located remote from the L-shaped channel 8 and a fluid tight seal is established between the inhaler and the dispersion chamber 3.

Many pharmaceutically active substances are hydroscopical. They are sensitive to humidity and must be kept in an environment with a stable humidity. In order to avoid moisture entering into the inhaler the chamber in which the inhaler is arranged is sealed against environmental air in an air tight manner. This sealing is broken when the device is activated for inhalation, i.e. when the dispersion chamber 3 is turned to the active position. When in the active position, an opening in the wall adjacent the first chamber 2 is opened and an air inlet 75 is created (FIG. 4). When inhalation has been completed and the dispersion chamber is turned and lowered into its retracted position, the opening or air inlet is closed again and the air tight sealing is achieved again.

As mentioned above, the first chamber 2 and the dispersion chamber 3 are movable and telescopically arranged in relation to each other. Guiding elements are preferably provided which guide the movement of the chambers in relation to each other. These guiding elements can be provided as a pin on the surface of one of the chambers and a corresponding groove provided on the surface of the wall of the other chamber. The function of the guiding means will be further described below in relation to the function of the device.

The dispersion chamber 3 is arranged inside the first chamber 2 so that the bottom wall 35 of the dispersion chamber defines the top wall of the first chamber. A piston 4 is arranged inside the first chamber 2. The piston 4 is movable between a retracted first position and a released second position as can be seen in FIGS. 2 and 3 respectively. The piston 4, the wall 35 and the sides of the first chamber 2, together define a suction chamber. The volume of the suction chamber is varied by the movement of the piston. The piston 4 is provided with a seal 41 providing a fluid tight seal against the walls of the first chamber during most of the movement of the piston. Between the bottom wall 35 of the dispersion chamber and the piston 4 biasing means 43 are provided which force the piston to its released second position when the piston is released from its retracted first position. The biasing means is preferably a spring. Lugs 42 are provided on the piston latching into grooves 21 provided on the bottom of the dispersion chamber 3 thereby holding the piston against the biasing force of the spring and locking it in its first position.

In order to achieve the optimum flow profile for the air and/or gas drawn through the inhaler where the flow rate increases in a controlled way to a maximum rate about 60 l/min, an air/gas flow regulating device 9 is arranged in the dispersion chamber 3. This compensates for the characteristics of the sprung device, i.e. the piston 4 and biasing means 43, described above.

The air regulating device is preferably constructed as a flow regulating valve 9 and is attached to the piston 4. The flow regulating valve 9 is formed as a needle valve having a stand pipe 91 and a cone shaped needle 92 arranged inside the stand pipe 91. The stand pipe is mounted in the bottom wall 35 of the dispersion chamber 3 and protrudes upwardly inside the dispersion chamber 3. A one way valve 93 is arranged at the upper part of the stand pipe allowing fluid, i.e. air or even gas, to enter into the stand pipe and down into the variable volume of the suction chamber (FIG. 4).

The cone shaped needle 92 is provided on the piston 4 and protrudes upwardly into the stand pipe 91. In the retracted first position of the piston 4, the needle 92 is provided inside the stand pipe along its whole length. When the piston is released from its retracted position and moves downwardly so as to increase the volume of the suction chamber, the needle will move with the piston and out of the stand pipe. The needle restricts the cross section of the stand pipe and thereby restricts the valve clearance in the stand pipe. The air flow down through the stand pipe is thus most restricted at the point of release of the piston, but this restriction will decrease as the needle moves downwardly out of the stand pipe and into the first chamber. In order to make the most optimal use of the inhaler arranged inside the device, the air flow during the suction of air through the device should be the same every time the device is used. This can be achieved by the arrangement of the stand pipe and the needle. With the described construction, the speed, force and air flow profile of the air flow through the device is optimised. The shape and length of the needle 92 has been determined out of the object to achieve said optimised inhalation air flow.

Figure 7A:
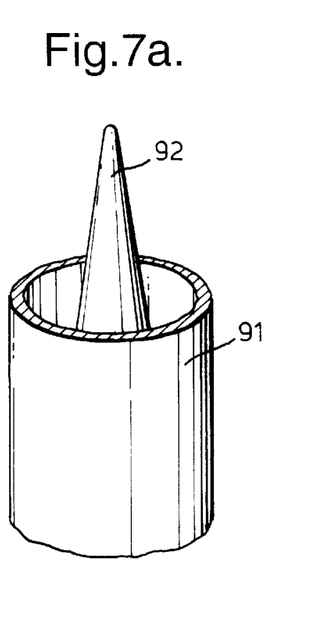
Figure 7B:
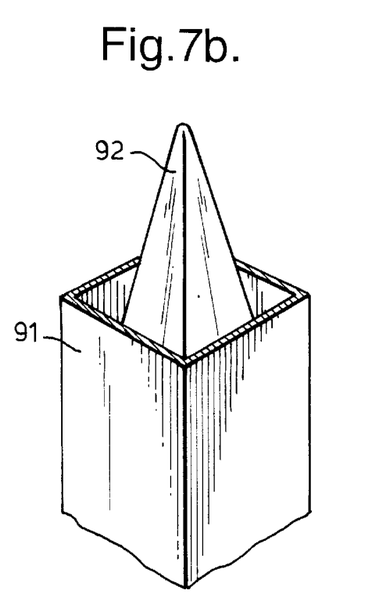
Figure 7C:
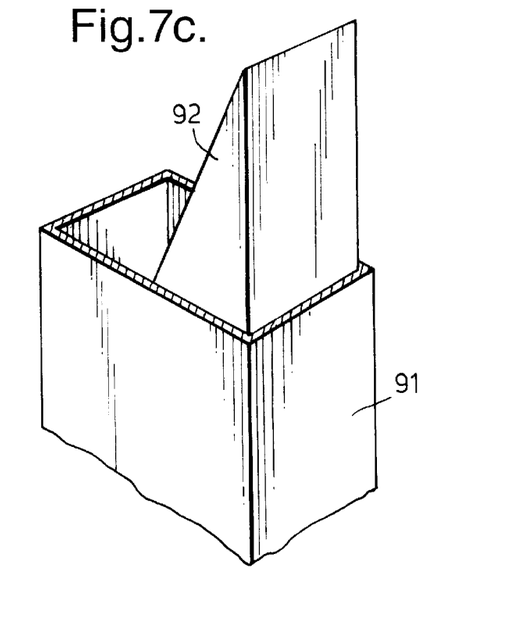
Figure 7D:
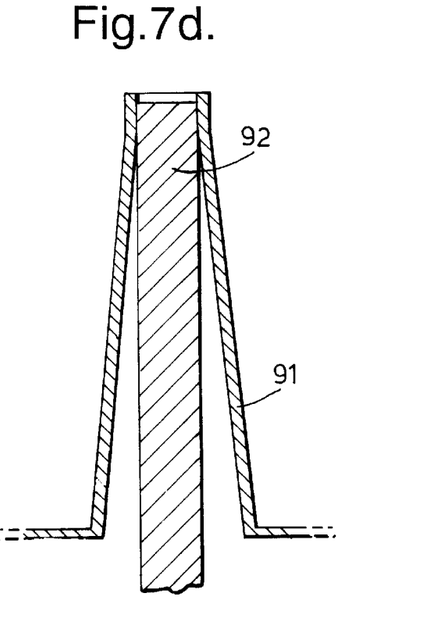
Figure 7E:
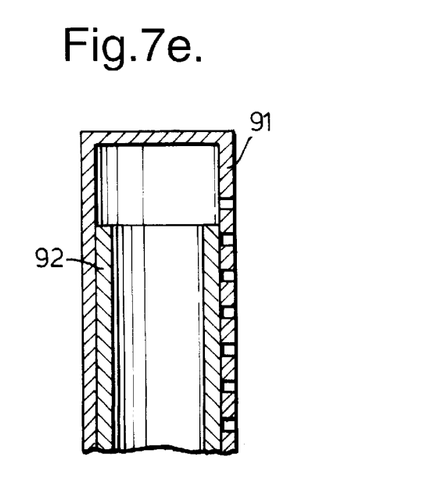
Figure 7F:
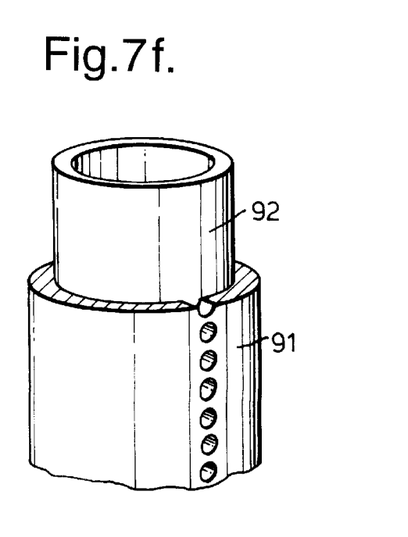

FIG. 7a illustrates a partial cross section through the standpipe 91 and shows the conical shape of needle 92. Of course, any other form with any other cross section could also be used as long as the requirement of flow restriction is achieved. Other possible valve arrangements are illustrated in FIGS. 7b to 7f. FIGS. 7b and 7c show variations on the embodiments of FIG. 7a. FIG. 7d shows a valve with a variable cross section standpipe. FIGS. 7e and 7f illustrate a valve having a hollow needle and a series of apertures down the side of the standpipe. For this latter embodiment, to avoid dispersed substance being drawn into the standpipe, the device of FIGS. 1 to 4 should preferably be modified to move the dispersion chamber inlet away from the series of apertures. These and other suitable regulating valves can be used with other dispersion chambers such as described above in conjunction with EP-A-0548152.

The mounting and activating means 6 mentioned above comprises a shaft, having a square or rectangular cross section 11, mounted in the bottom wall of the housing 1 and protruding into the first and dispersion chambers 2, 3 through holes 44 and 36 arranged in the piston and the bottom wall 35 of the dispersion chamber respectively.

Figure 8A:
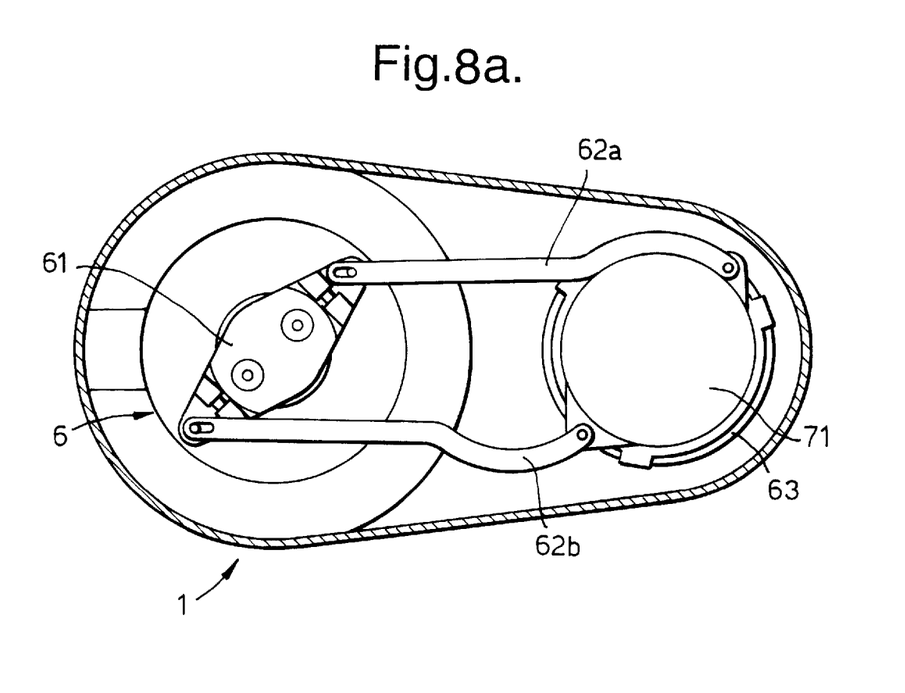
Figure 8B:
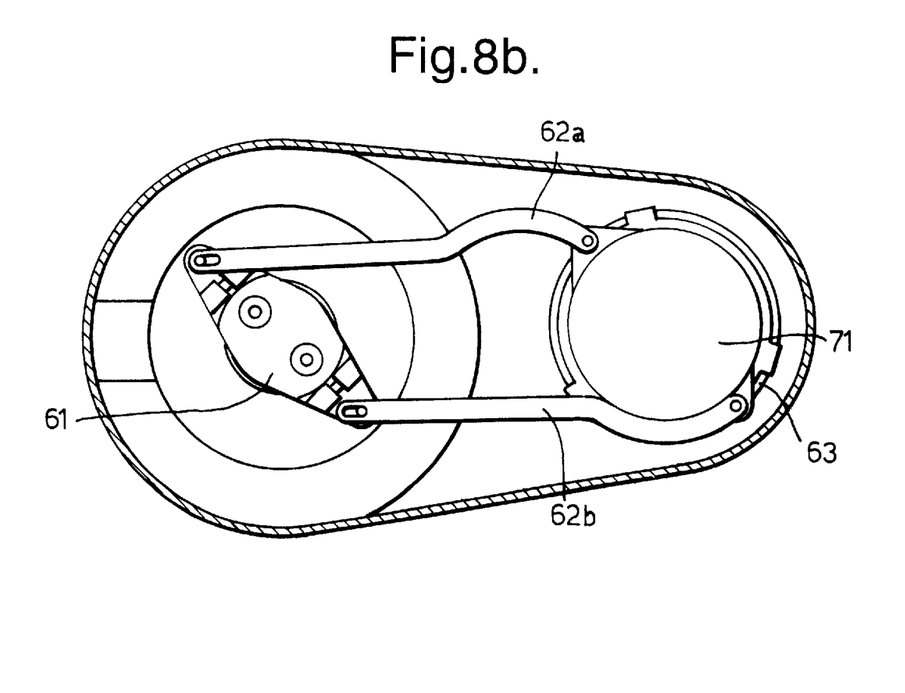

According to one embodiment, a lever 61 is connected to the shaft 11 at its lower end. As illustrated in FIGS. 8a and 8b, at least one, preferably two, further levers 62a, 62b are connected to the first lever 61 at their first ends. The second ends of these further levers 62a, 62b are connected to a mounting element 63 in which the manoeuvring means 71 of the inhaler 7 is arranged. The further levers are connected to the mounting element 63 in such a manner that movement of the levers 62a and 62b will cause the mounting element 63 to turn, whereby the manoeuvring means 71 of the inhaler will also be turned. The turning movement of the manoeuvring means 71 corresponds to the required movement of the means for feeding a dose into the inhalation channel of the inhaler. The length and form of the further levers is determined by the required turning movement of the manoeuvring means 71.

Figure 9:
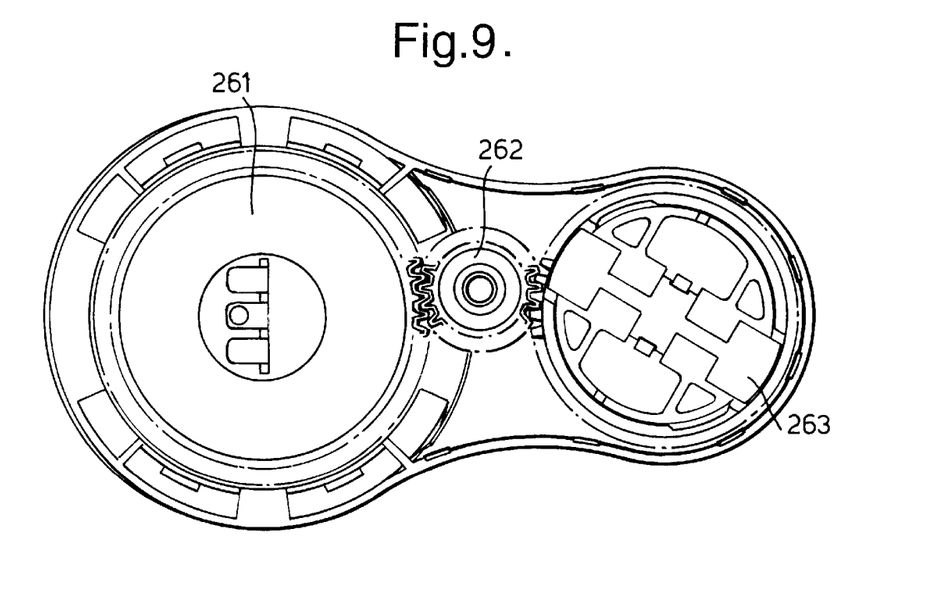

An alternative embodiment is illustrated in FIG. 9. In this embodiment a gear 261 is connected to the shaft 11 at its lower end. The gear 261 is then connected via an intermediate gear 262 to a mounting gear 263 which is attached to an integral part of mounting element 63.

The function of the device will now be described.

Initially the inhalation device is in the position shown in FIG. 1 with the dispersion chamber 3 retracted into the first chamber 2 and with the mouth piece 32 placed in its retracted position. When the user is to inhale, the dispersion chamber is raised in relation to the first chamber 2 as shown in FIG. 1. Thereafter, the mouth piece 32 is turned by an angle of about 90° from its inactive to its active position. In the preferred embodiment, the mouth piece 32 is mounted to or formed as a part of the lid 31 and the lid 31 which is rigidly connected to or formed as a part of the upper part of the dispersion chamber 3. The movement of the mouth piece 32 will release the locking means of the piston 4 from its first locked position.

In the preferred embodiment, the dispersion chamber 3 is rotated by about 90° in a plane parallel to the horizontal as illustrated in the Figures, but the angle can be made less or more than 90° simply by modifying the arrangement of the lever arms or the number of gear teeth in the mounting and activating means 6. This is because the turning movement of the manoeuvring means 71 to feed a dose to its release position determines the required movement of the mounting element 63. The mounting element 63 is turned by the movement of the lever arms 61, 62a and 62b or the gears 261, 262, 263 when the device is activated, i.e. when the dispersing chamber 3 and the mouth piece 32 are turned.

When the lid 31 and the mouth piece 32 are turned to activate the inhalation device, the movement of the dispersion chamber 3 and the piston 4 is transferred to the first lever 61 or gear 261 via the shaft 11. The first lever 61 turns and transfers this movement to the further levers 62a and 62b or the gear 261 transfers this movement to gears 262, 263 which then turn the mounting element 63 and the manoeuvring means 71 of the inhaler 7.

As described above the mounting and activating means 6 for the inhaler is arranged in such manner that the manoeuvring means 71 of the inhaler 7 is turned when the mouth piece 32 is turned to its active position. In this way a dose of the substance to be inhaled will be fed from the reservoir of the inhaler into the dosing unit and positioned for inhalation in the inhalation channel of the inhaler.

In the initial retracted position, the lugs 42 of the piston 4 are latched into the locked position in the bottom wall 35 of the dispersion chamber. When the dispersion chamber is moved in relation to the first chamber, the piston 4 will follow the dispersion chamber upwardly until an end position is reached. When the end position has been reached, the mouth piece is turned and the arrangement of the guiding means between the two chambers will unlock the lugs 42 such that the piston 4 is released. Due to the biasing forces of the spring 43, the piston is forced downwardly away from wall 35 inside the first chamber increasing instantly the volume of the suction chamber. A negative pressure or vacuum is thus created in the suction chamber. Through the stand pipe 91, air is drawn from the dispersion chamber down into the suction chamber and a negative pressure or vacuum is created in the dispersion chamber. As mentioned above, air inlets 75 are arranged in the bottom wall of the housing 1. These air inlets are formed to guide air/gas in to the chamber in which the inhaler is housed. Due to a seal 73 provided around the inhaler, the only path for the air is through the inhalation channel of the inhaler. A dose of the powder has already been placed in the inhalation channel during the activation of the device. This dose will be lifted out of its position, mixed with the air in the air flow and will travel with the air flow up through the mouth piece 72 of the inhaler via the L-shaped connection means 8 into the dispersion chamber through the opening 34.

Figure 10:
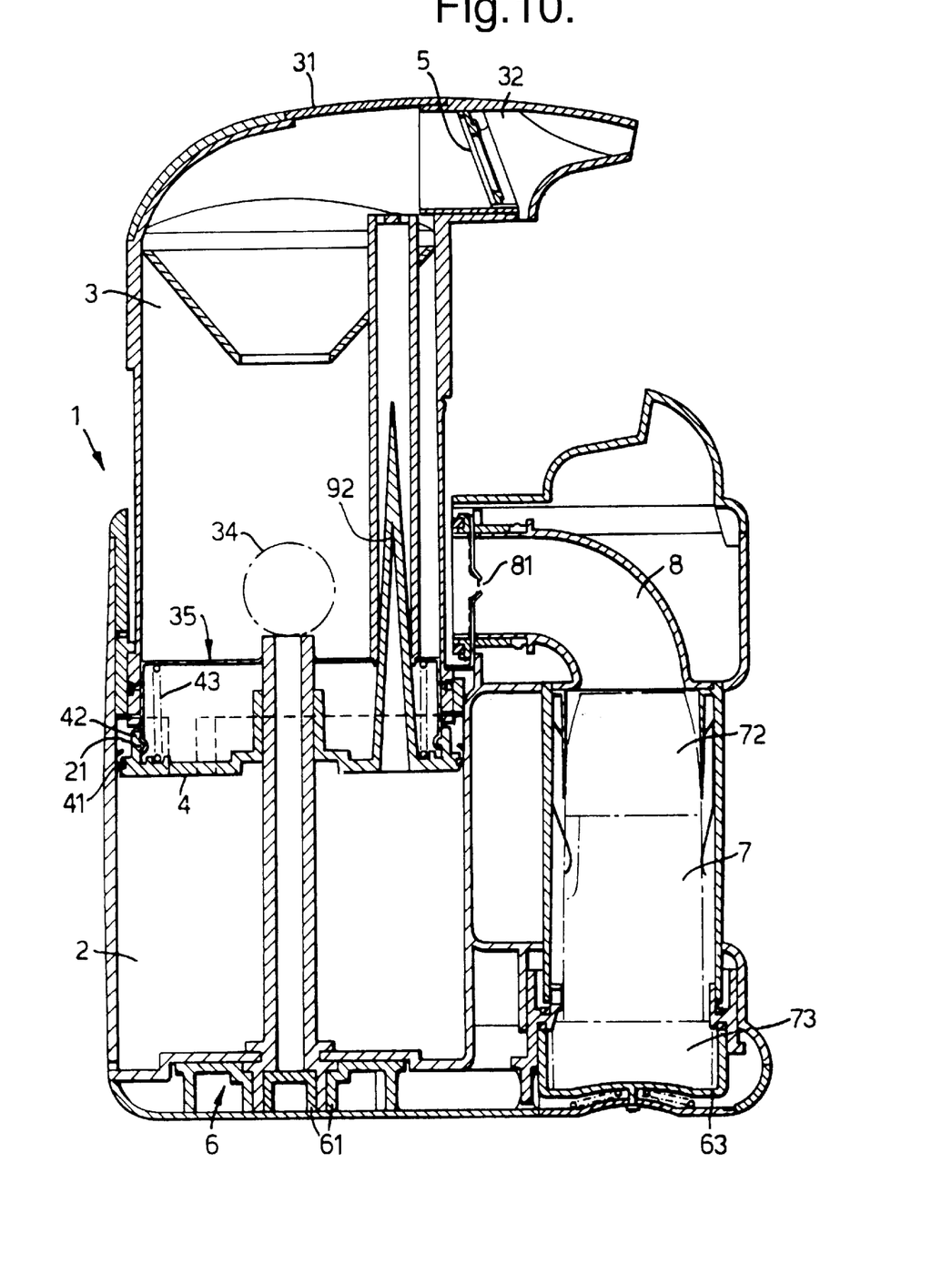
Figure 11A:
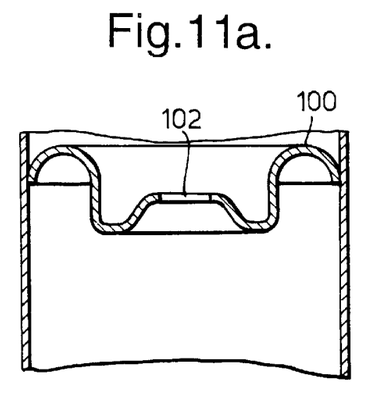
Figure 11B:
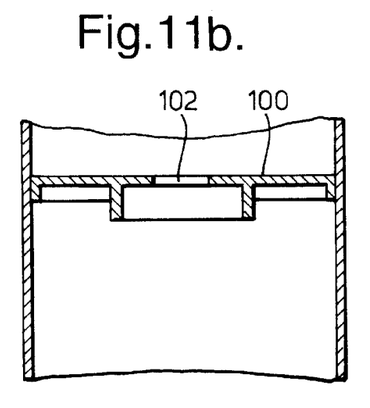

The stand pipe 9 is constructed in such a manner that the volume of air passing down to the suction chamber is less then the air volume of the dispersion chamber before air is entered from the inhaler. In this manner the amount of aerosolised substance which enters into the stand pipe is minimised.

As illustrated in FIG. 10, in order to further improve the device, an insert 100 can be provided in said dispersion chamber 3 in order to provide a channelled region and to prevent powder particles which have collected on the bottom of the dispersion chamber from falling out of the dispersion chamber into the inhalation channel 33 of the lid or into the mouth piece 32. Preferably, the insert 100 has a funnel-form and is placed with its tip directed downwardly towards the bottom 35 of the dispersion chamber 3. However, any form producing a channelled region around the outlet 102 will have an equivalent effect, such as a curved cross section as illustrated in FIG. 11a and a ridge as illustrated in FIG. 11b. These channelled regions may be used with other dispersion chambers such as described above in conjunction with EP-A-0548152.

Possible Modifications

The inhalation device according to the invention as described above could of course be modified within the scope of the appended claims.

Thus, although in the preferred embodiment, the mouth piece and the dispersing chamber are turned through an angle of about 90° when the device is activated for inhalation, by a modification of the guiding means, the angle of rotation can be changed to any other desirable angle.

Although a breath-actuated dry-powder inhaler has been described above, any other inhaler could be used where a dose of a substance to be inhaled is placed in an inhalation channel for inhalation and in which air or gas is drawn through the inhalation channel in order to mix the dose with the inhalation flow and to transport it to a patient.

The device has been described for use with air drawn from the environment around the device. However, if necessary or required, a gas source could easily be connected to the air inlet of the device and gas could be drawn into the device instead of or together with outside ambient air.

It is also possible to modify the device so that the air contained in the chamber 2 under the piston 4 is used to equalize the negative pressure or vacuum created in the inhaler during the drawing of air from the inhaler into the dispersing chamber 3. In this case, air from the chamber 2 will be drawn through air inlets close to the inhaler and will pass through the inhaler in the same manner as described above. An advantage of this arrangement is that the increased pressure created in the air volume beneath the piston provides an extra force to release and transport the dose and the air up through the inhaler and further into the dispersion chamber.

In the described embodiment, the mounting and activating means consists of a lever mechanism comprising lever arms or a gear drive. However, other activating mechanisms for the manoeuvring means of the inhaler could be used, such as different types of drive mechanisms, e.g. drive belts and similar.

What is claimed is:

1. An inhalation device in combination with an inhaler, the device comprising:
    an inhaler chamber receiving said inhaler;
    a dispersion chamber constructed for fluid communication with the inhaler chamber so as, in use, to receive a substance to be inhaled from said inhaler; and
    a suction chamber of variable internal volume in fluid communication with said dispersion chamber, said suction chamber being constructed to enable the internal volume of said suction chamber to be increased during use, producing a negative pressure in said dispersion chamber, thereby drawing the substance to be inhaled from the inhaler chamber into the dispersion chamber for subsequent inhalation,
    said dispersion chamber being telescopically mounted for sliding within said suction chamber.

2. The inhalation device of claim 1 wherein said suction chamber comprises a first chamber and a piston movable within said first chamber.

3. The inhalation device and inhaler of claim 1, wherein the substance is a pharmaceutically active substance.

4. The inhalation device of claim 1, wherein said inhaler is a dry-powder inhaler.

5. The inhalation device of claim 1 further comprising a section adapted to receive a portion of the inhaler in communicating relation.

6. The inhalation device of claim 5 wherein said section communicates with said dispersion chamber.

7. The device and inhaler of claim 1, wherein the dispersion chamber has a substantially constant volume.

8. The device and inhaler of claim 1, wherein the device is configured such that during use, the substance is drawn from said inhaler in the inhaler chamber into the dispersion chamber without passing into the suction chamber.

9. The device and inhaler of claim 1, further comprising a mouthpiece in fluid communication with the dispersion chamber, wherein during use, the substance drawn into the dispersion chamber is inhaled from the dispersion chamber through the mouthpiece.

10. An inhalation device in combination with an inhaler, the device comprising:
    an inhaler chamber receiving for said inhaler;
    a dispersion chamber constructed for fluid communication with the inhaler chamber so as, in use, to receive a substance to be inhaled from said inhaler; and
    a suction chamber of variable internal volume in fluid communication with said dispersion chamber, said suction chamber being constructed to enable the internal volume of said suction chamber to be increased during use, producing a negative pressure in said dispersion chamber, thereby drawing the substance to be inhaled from the inhaler chamber into the dispersion chamber for subsequent inhalation,
    wherein said suction chamber comprises a first chamber and a piston movable within said first chamber,
    wherein the dispersion chamber is mounted telescopically within said first chamber and is movable between a retracted position within said first chamber and an extended position.

11. The inhalation device and inhaler of claim 10 wherein said dispersion chamber has a wall dividing it from said first chamber, said piston being releasably connected adjacent said wall and movable with said dispersion chamber when connected.

12. The inhalation device and inhaler of claim 11 further comprising a releasing mechanism for releasing the connection with said piston and a biasing member for biasing said piston away from said wall wherein when said dispersion chamber is moved from a retracted position to an extended position, the piston moves with the dispersion chamber until the dispersion chamber reaches the extended position, whereupon the releasing mechanism operates to release the connection with the piston, such that the piston is biased away from the wall and the internal volume of said suction chamber is increased.

13. An inhalation device in combination with an inhaler, the device comprising:
    an inhaler chamber receiving said inhaler;
    a dispersion chamber constructed for fluid communication with the inhaler chamber so as, in use, to receive a substance to be inhaled from said inhaler; and
    a suction chamber of variable internal volume in fluid communication with said dispersion chamber, said suction chamber being constructed to enable the internal volume of said suction chamber to be increased during use, producing a negative pressure in said dispersion chamber, thereby drawing the substance to be inhaled from the inhaler chamber into the dispersion chamber for subsequent inhalation, further comprising an element for controlling the fluid flow from said dispersion chamber to said suction chamber.

14. The inhalation device and inhaler of claim 13, wherein said element comprises a fluid regulating valve.

15. The inhalation device and inhaler of claim 13, wherein said suction chamber comprises a first chamber and a piston movable within said first chamber, and said element comprises a stand pipe and a cone-shaped restriction element on said piston protruding into the inside of said stand pipe, said cone-shaped restriction being constructed to regulate the fluid flow through the stand pipe.

16. An inhalation device in combination with an inhaler, the device comprising:

an inhaler chamber receiving said inhaler;

a dispersion chamber constructed for fluid communication with the inhaler chamber so as, in use, to receive a substance to be inhaled from said inhaler; and a suction chamber of variable internal volume in fluid communication with said dispersion chamber, said suction chamber being constructed to enable the internal volume of said suction chamber to be increased during use, producing, a negative pressure in said dispersion chamber, thereby drawing the substance to be inhaled from the inhaler chamber into the dispersion chamber for subsequent inhalation, wherein said suction chamber comprises a first chamber and a piston movable within said first chamber, wherein the inhaler includes a maneuvering element for feeding a dose of the substance to an inhalation channel of the inhaler, and the device further comprises a mounting and activating member comprising a mounting element for mounting the maneuvering element and a lever arrangement movably connected to the mounting element and connected to the first chamber and dispersion chamber.

17. The inhalation device and inhaler of claim 16, further comprising a shaft connected to the lever arrangement and mounted on a bottom wall of said dispersion chamber and said piston, whereby a movement of said dispersion chamber and first chamber in relation to the inhaler is transferred to the maneuvering element via said shaft and said lever arrangement.

18. An inhalation device in combination with an inhaler, the device comprising:

an inhaler chamber receiving said inhaler;

a dispersion chamber constructed for fluid communication with the inhaler chamber so as, in use, to receive a substance to be inhaled from said inhaler; and a suction chamber of variable internal volume in fluid communication with said dispersion chamber, said suction chamber being constructed to enable the internal volume of said suction chamber to be increased during use, producing a negative pressure in said dispersion chamber, thereby drawing the substance to be inhaled from the inhaler chamber into the dispersion chamber for subsequent inhalation, wherein said suction chamber comprises a first chamber and a piston movable within said first chamber, wherein the inhaler includes an inhalation channel and a maneuvering element for feeding a dose of the substance to said inhalation channel, and the inhalation device further comprises a mounting and activating member comprising a gear arrangement in moveable connection with a mounting element wherein said gear arrangement is connected to the first chamber and dispersion chamber.

19. An inhalation device in combination with an inhaler, the device comprising:

an inhaler chamber receiving said inhaler;

a dispersion chamber constructed for fluid communication with the inhaler chamber so as, in use, to receive a substance to be inhaled from said inhaler; and a suction chamber of variable internal volume in fluid communication with said dispersion chamber, said suction chamber being constructed to enable the internal volume of said suction chamber to be increased during use, producing a negative pressure in said dispersion chamber, thereby drawing the substance to be inhaled from the inhaler chamber into the dispersion chamber for subsequent inhalation, further comprising a funnel-shaped insert disposed within said dispersion chamber, said funnel-shaped insert having a base that contacts a wall of said dispersion chamber, and an open tip, said open tip defining an inhalation outlet for said dispersion chamber, wherein said funnel-shaped insert extends from said base to said open tip in a direction generally opposite the direction of air flow through said dispersion chamber during inhalation.

20. A method of preparing a substance in a dispersed state in a dispersion chamber, said method comprising the steps of:

providing a dispersion chamber having structure thereon adapted for fluid connection to a patient's respiratory tract;

providing a suction chamber having a variable internal volume in fluid connection with the dispersion chamber;

said dispersion chamber being telescopically mounted for sliding within said suction chamber;

providing a dispenser having a substance therein in fluid connection with the dispersion chamber;

producing a negative pressure within said variable internal volume of the suction chamber and drawing the substance from the dispenser into the dispersion chamber by increasing the variable internal volume of the suction chamber.

21. The method of claim 20, wherein a volume of the dispersion chamber remains substantially constant during the increasing step.

22. The method of claim 20, wherein, in use, the substance is drawn from an inhaler in the inhaler chamber into the dispersion chamber without passing into the suction chamber.

23. An inhalation device comprising:

a dispersion chamber for containing a substance dispersed in a gas;

a sprung device for creating a change in pressure so as to cause said dispersed substance to flow into said dispersion chamber; and a flow regulating valve of variable restriction for restricting said flow of said dispersed substance into said dispersion chamber; wherein the restriction of said flow regulating valve is arranged to vary in conjunction with the operation of said sprung device so as to compensate for characteristics of the sprung device.

24. The inhalation device of claim 23 wherein said flow regulating valve is located at an outlet of said dispersion chamber.

25. The inhalation device of claim 23 wherein the sprung device comprises a moveable piston and a spring constructed to move said piston.

26. The inhalation device of claim 23 wherein the flow regulating valve comprises an elongate pipe and an axially moveable member within said pipe, the relative cross sections of the pipe and the member being such that as the member is moved axially out of the pipe, the cross sectional area between the pipe and the member increases.

27. A method of preparing a substance in a dispersed state in a dispersion chamber comprising:

operating a sprung device to create a change in pressure so as to cause said dispersed substance to flow into said dispersion chamber through a stand pipe;

varying the location of a restriction means disposed within said stand pipe to vary a restriction offered to the flow into the dispersion chamber in conjunction with operation of said sprung device.

28. An inhalation device for providing a substance dispersed in a gas for inhalation, the device comprising:

walls defining a dispersion chamber for containing dispersed substance and defining an outlet in said dispersion chamber through which said dispersed substance may leave said dispersion chamber in a dispersed state; wherein said walls also define at least one channeled region at least partly surrounding said outlet and comprising a flanged portion extending inwardly from said walls such that any substance on said walls cannot be caused to travel across the walls defining said channeled region and to pass through said outlet.

29. The inhalation device of claim 28 wherein said walls defining said channelled region comprise a substantially conical section extending in a first direction from a base to a tip, said tip defining said outlet of the dispersion chamber, wherein said first direction is generally opposite the direction of air flow through said dispersion chamber during inhalation.

30. A method of preparing a substance in a dispersed state in a dispersion chamber and of preventing the substance from exiting the dispersion chamber via an outlet of the dispersion chamber when the substance is not in a dispersed state, the method comprising:

providing walls in said dispersion chamber which define at least one channeled region at least partly surrounding said outlet, wherein said channeled region comprises a flanged portion extending inwardly from said walls.

* * * * *

UNITED STATES PATENT AND TRADEMARK OFFICE
CERTIFICATE OF CORRECTION

PATENT NO. : 6,286,506 B1
DATED : September 11, 2001
INVENTOR(S) : John MacAndrew, William Revell, Paul Robertson, Elna Berg and Magnus Jeppsson It is certified that error appears in the above-identified patent and that said Letters Patent is hereby corrected as shown below:

<u>Title page,</u>
Item [30], Foreign Application Priority Data, "9503344" should be -- 9503344-5 --

Item [56], References Cited, U.S. PATENT DOCUMENTS, insert:
    -- 5239992  8/93  Bougamont et al. --
    -- 5323936  6/94  Wolter et al. --

<u>Drawings,</u>
Fig. 10 insert -- 100 -- and -- 102 -- as included on the substitute Fig. 10 attached.

<u>Column 1,</u>
Line 43, insert -- ; -- before CFC

<u>Column 13,</u>
Line 3, insert -- ; -- after "wherein"

Signed and Sealed this

Twentieth Day of August, 2002

*Attest:*

JAMES E. ROGAN
*Attesting Officer*  *Director of the United States Patent and Trademark Office*

Fig. 10.